United States Patent [19]

Segal et al.

[11] Patent Number: 4,922,914
[45] Date of Patent: May 8, 1990

[54] DISPOSABLE COVER FOR TONOMETER

[76] Inventors: Elizabeth O. Segal; William R. Segal, both of 1503 Marker Rd., Middletown, Md. 21769

[21] Appl. No.: 187,563

[22] Filed: Apr. 28, 1988

[51] Int. Cl.$^5$ .............................................. A61B 3/16
[52] U.S. Cl. .................................. 128/646; 206/608; 206/461
[58] Field of Search ............... 128/645, 646, 652, 647, 128/346; 600/5; 206/438, 363, 370, 608, 610, 611, 467, 471, 461; 285/332

[56] References Cited

U.S. PATENT DOCUMENTS

| | | | |
|---|---|---|---|
| 3,338,090 | 8/1967 | Coombs, Jr. et al. | 128/652 |
| 3,426,749 | 2/1969 | Jephcott | 206/363 |
| 3,794,091 | 2/1974 | Ersek et al. | 128/6 |
| 4,197,947 | 5/1980 | Zaidi | 206/438 |
| 4,511,035 | 4/1985 | Alpern | 206/363 |
| 4,662,360 | 5/1987 | O'Hara et al. | 128/664 |
| 4,669,610 | 6/1987 | Lindsey et al. | 206/471 |
| 4,730,726 | 3/1988 | Holzwarth | 206/471 |
| 4,790,569 | 12/1988 | Chaffee | 285/255 |

OTHER PUBLICATIONS

Mackay et al., "Fast Automatic Ocular Pressure Measurement Based on an Exact Theory", IEEE Transactions on Medical Electronics, pg. 60.

Primary Examiner—Max Hindenburg
Assistant Examiner—S. Getzow
Attorney, Agent, or Firm—Morton J. Rosenberg; David I. Klein

[57] ABSTRACT

A disposable protective cover (100) for application to an applanation tonometer head (20) of a Goldmann-type applanation tonometer (10). The disposable protective cover (100) may be bag like in contour or preferably pre-formed into a frusto-conical contour having a planar surface (102) bounded by a conical surface (104) which substantially matches the planar surface (22) and the conical surface (24) of applanation tonometer head (20). Disposable protective cover (100) includes at least one tab member (130) for use in handling tonometer cover (100) during application and removal therefrom. Protective cover (100) in general and the planar surface (102) in particular must fit tightly to applanation head (20), be optically transparent, and sufficiently thin so as not to interfere with the tonometer measurement. Protective cover (100) is releasably secured to applanation head (20) by a double-backed removable adhesive strip (140) which is located on the conical surface (24) of applanation tonometer head (20).

14 Claims, 3 Drawing Sheets

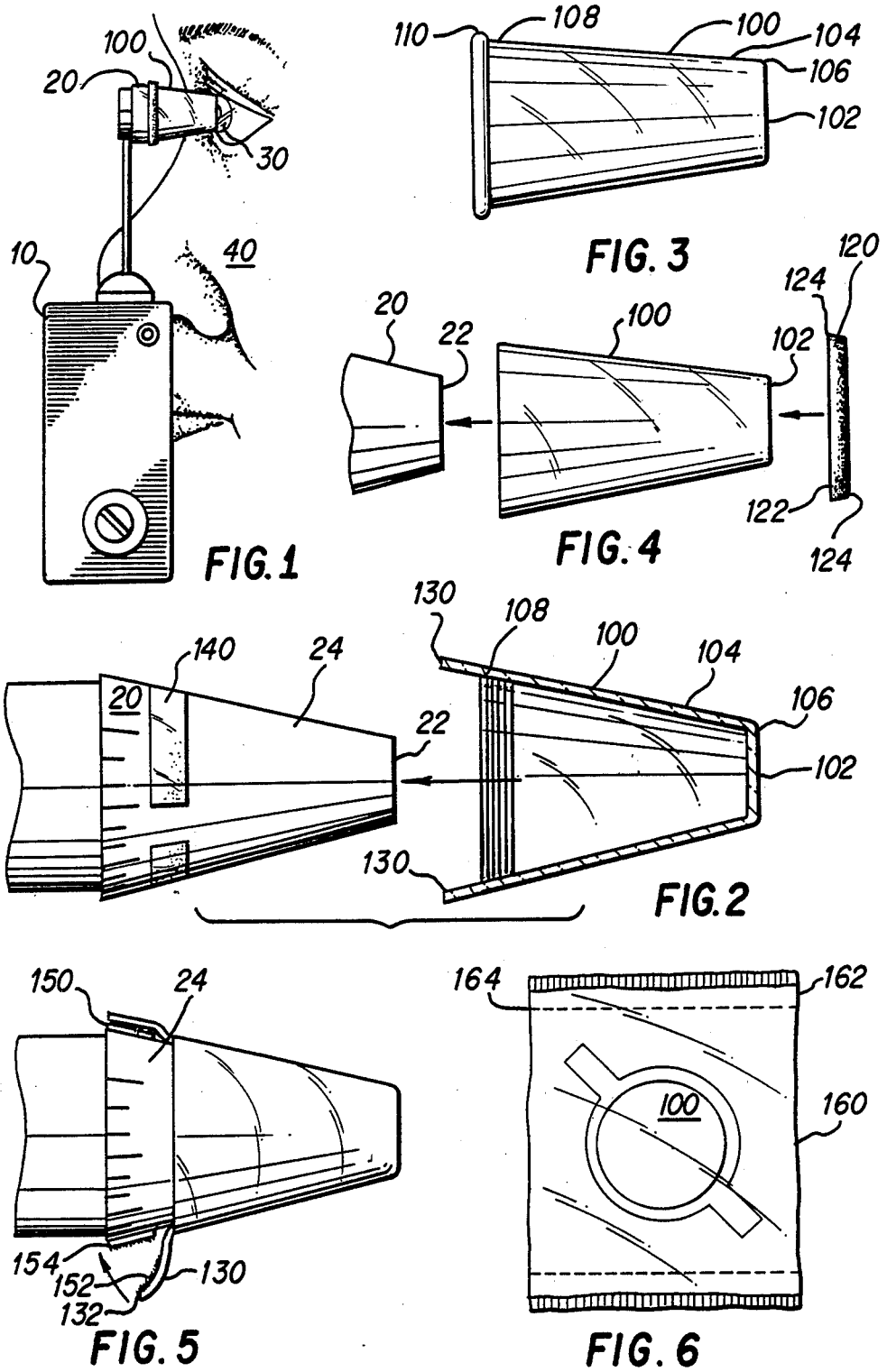

DISPOSABLE COVER FOR TONOMETER

BACKGROUND OF THE INVENTION

1. Field of the Invention

This invention directs itself to a disposable protective cover for use with a Goldmann-type applanation tonometer, as well as a kit type package for providing the cover. In particular, this invention directs itself to a disposable cover which may in general be described as a condom like cover member having an overall bag contour or in order to interface in a more contiguous manner may be pre-formed into a frusto-conical contour, formed from an optically transparent material which is sufficiently thin so as not to interfere with the tonometer measurement. More in particular, this invention pertains to a disposable protective cover having at least one tab member for use in handling the cover during application to and removal from the tonometer head. Further, this invention directs itself to a kit for providing a sterile tonometer cover which is formed in one wall of the package.

2. Prior Art

Disposable tonometers, and disposable tonometer covers, are well-known in the art. The best prior art known to the Applicants include U.S. Pat. Nos. 1,743,461; 2,780,221; 2,984,099; 3,049,001; 3,272,001; 3,282,090; 3,330,152; 3,338,090; 3,376,735; 3,443,421; 3,511,085; 3,714,819; 4,213,464; and, 4,593,699.

Some prior art systems, like that shown in U.S. Pat. No. 4,213,464 are directed to tonometer transducer assemblies which have provisions for a removable and interchangeable membrane seal. Such membrane seals are formed from resilient material, but must be retained to the conical surface of the transducer by an O-ring which fits in an annular groove formed in the surface of the transducer. However, the annular groove does not exist in the current Goldmann-type applanation tonometers in use today, therefore, the tonometer heads would require modification or replacement for use of this type prior art system. In contradistinction, the present invention is retrofittable in existing Goldmann-type tonometer heads without modification thereto.

In other prior art systems, such as U.S. Pat. Nos. 3,049,001, and 3,272,001, there are provided tonometer systems having protective sheaths placed over the end of the tonometer. Although these sheaths may provide a sterile contact for the instrument on the cornea of the eye, they are used on tonometer heads which include a cylindrical portion to which the sheath can frictionally retain itself. In addition, these prior art systems are not used in conjunction with optical instruments and therefore do not require the sheath to be formed from an optically transparent material, whose compositions typically do not exhibit the elasticity required to form a sheath which is frictionally self-retaining, as required by the systems in the prior art. Therefore, substitution of materials alone would not render the prior art system devices usable with the Goldmann-type applanation tonometer. In still other prior art devices, such as U.S. Pat. No. 3,338,090, make use of a replaceable tip for an applanation tonometer which is optically transparent. However, such tips are held to the applanation head by either a magnetized collar or a spring clip arrangement. Obviously, these replaceable tips as disclosed in the prior art are far more costly and complex than the condom like tip member or preformed membrane-like cover of the subject invention. Additionally, the covers as disclosed in the prior art are not adaptable for retention on the conical surface of the currently used Goldmann-type applanation tonometer. Further, the covers of the prior art do not provide for a means of handling the cover during application to the tonometer head and removal therefrom, as provided by the subject invention.

SUMMARY OF THE INVENTION

A disposable protective cover for application to the frusto-conical contour of an applanation tonometer head. The disposable protective cover comprises a sheath member having a predetermined contour to contiguously interface with the tonometer head. The sheath member is formed from a substantially optically transparent composition having a predetermined thickness so as to minimize interference with the tonometer measurement. The diposable protective cover also includes a means for releasably retaining the sheath member to the conical surface of the tonometer head.

An object of the subject invention concept is to provide a disposable protective cover for the Goldmann-type applanation tonometer as provided in U.S. Pat. No. 3,070,997. The Goldmann-type tonometer system includes a conical surface contour which is particularly difficult for attachment cover retentions. The subject concept provides for a cover member which maintains the optical integrity necessary while simultaneously allowing an easily removable and insertable cover system.

BRIEF DESCRIPTION OF THE DRAWINGS

FIG. 1 is an elevation view showing an applanation tonometer in use;

FIG. 2 is an elevation view, partially in cut-away showing the tonometer head and protective cover therefor;

FIG. 3 is an elevation view of an alternate embodiment of the protective cover shown in FIG. 2;

FIG. 4 is an elevation view of another alternate embodiment of the protective cover shown in FIG. 2;

FIG. 5 is an elevation view showing an alternate embodiment for the retaining means shown in FIG. 2;

FIG. 6 is a plane view of a package for the protective cover;

DESCRIPTION OF THE PREFERRED EMBODIMENTS

Figure 7:
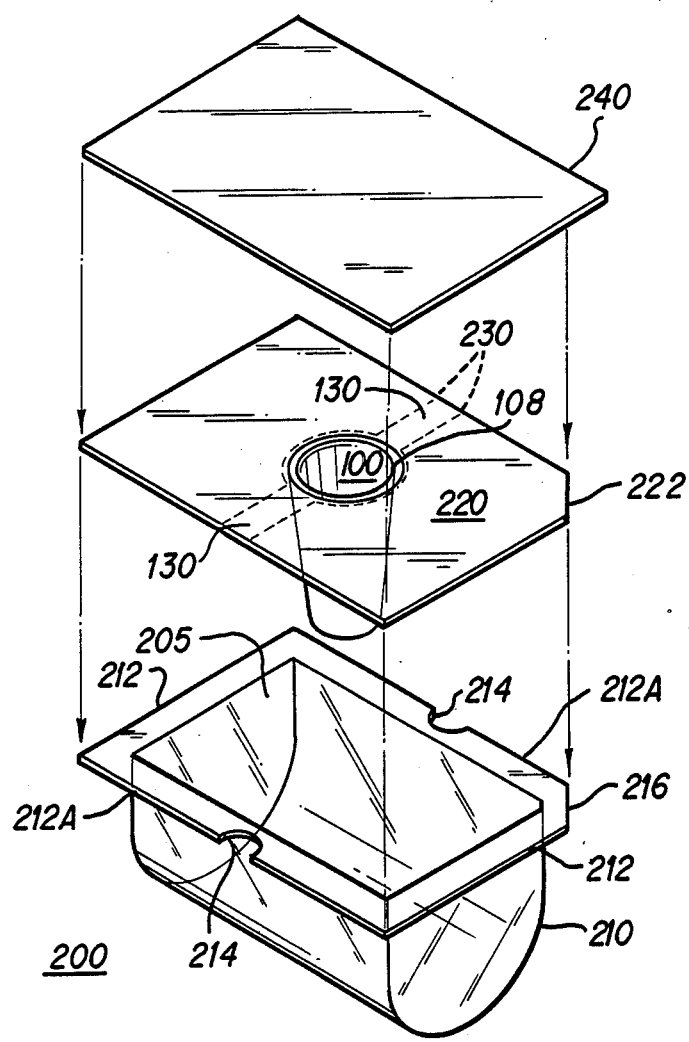
FIG. 7 is an exploded view of a sterile protective cover kit.

Referring now to FIG. 1, there is shown disposable protective cover 100 for application to an applanation tonometer head 20 so as to isolate tonometer head 20 from direct contact with patient 40. Thus, by discarding the disposable protective tonometer cover 100 after use on a first patient 40, then replacing it with a fresh disposable, tonometer cover 100 for use with a second patient 40, the likelihood of transmitting a communicable disease from one patient 40 to another with the applanation tonometer 10 is extremely small. As will be seen in following paragraphs, disposable tonometer cover 100 is directed to the concept of providing a protective sheath for use on the tonometer head 20 of the Goldmann-type applanation tonometer. Additionally, disposable protective tonometer cover 100 must be adapted to fit the frusto-conical contour of the Goldmann-type applanation tonometer head 20, must be optically transparent, and have a wall thickness sufficiently thin so as to minimize interference with the tonometer measurement.

Measurement of intraoccular pressure using the Goldmann applanation tonometer 10, shown in FIG. 1, provides a very accurate measurement which is used as an aid in the diagnosis of glaucoma. The applanation head 20 with disposable protective tonometer cover 100 located thereon is put in contact with cornea 30, sufficient force to flatten the corneal surface is applied while the physician views the patient's cornea through a slit lamp biomicroscope (not shown). It is important that disposable protective tonometer cover 100 not interfere with the accuracy of the tonometer instrument or the measurement obtained therefrom, consequently, disposable protective tonometer cover 100 must be (1) adapted to tightly fit the corneal contact surface 22 (shown in FIG. 2), of applanation head 20, (2) formed of an optically transparent material to permit viewing of the cornea by the physician, and, (3) have a material thickness which has been predetermined to minimize any interference with the pressure measurement when tonometer cover 100 is utilized.

Referring now to FIG. 2, there is shown tonometer cover 100 having been preformed into a frusto-conical contour with a planar surface 102 at a first end 106 bounded by a conical surface 104, however, it is to be specifically understood that cover 100 may be generally condom tip like in contour with the important consideration being a reasonably close interface between the cooperating members. Conical surface 104 extends from first end 106 to second end 108. At least one tab member 130 extends from second end 108 for use in handling tonometer cover 100 for application to the applanation tonometer head 20 and removal therefrom. As will be described in following paragraphs, tab members 130 may form part of the retention system for securing tonometer cover 100 to applanation tonometer head 20.

As is shown in FIG. 2, the frusto-conical contour of applanation tonometer cover 100 has been dimensioned to substantially match the contour of applanation tonometer head 20 such that the substantially planar surface 102 of applanation tonometer cover 100 will fit tightly over the contact surface 22 of applanation tonometer head 20, which is similarly substantially planar in contour. The substantially planar contact surface 22 of applanation tonometer head 20 is bounded by a conical surface 24 to which conical surface 104 of applanation tonometer cover 100 has been adapted to provide a contiguous interface therewith.

It is important that applanation tonometer cover 100 be maintained securely to the applanation head 20 during the tonometer test. To this end, a double-backed removable adhesive strip 140 is first applied to the conical surface 24 of applanation tonometer head 20. Using tabs 130, applanation tonometer cover 100 is slipped over applanation head 20 until the planar surface 102 of applanation tonometer cover 100 is tautly engaged with substantially planar surface 22 of applanation head 20. Slight pressure may then be applied to the conical surface 104 of tonometer cover 100 in the area above the double-backed removable adhesive strip 140 located on the conical surface 24 of applanation tonometer head 20. The removable adhesive on the external surface of tape strip 140 insures that tonometer cover 100 is retained in position during the tonometer test.

Upon completion of the performance of a tonometer test on a patient, the tonometer cover 100 is removed from the applanation tonometer head 20 and replaced with a new tonometer cover 100 in preparation for testing a second patient. Tonometer cover 100 is easily removed from applanation head 20 by grasping tab members 130 and pulling the cover 100 from applanation head 20. The adhesive selected for use on double-backed strip 140 has been selected to be easily removable, such that tonometer cover 100 easily separates from the applanation head 20. Similarly, the double-backed adhesive strip 140 is easily removed from the applanation head 20 and replaced with a fresh strip prior to application of a new tonometer cover 100.

Referring now to FIG. 3, there is shown an alternate embodiment for applanation tonometer cover 100, having a retention ring 110 integrally formed therein. Retention ring 110 is located at second end 108 and bonded thereto to form an integral structure. Retention ring 110 is formed of an elastomeric material which is bonded to second end 108 of tonometer cover 100 by adhesive means, heat sealing, or like technique.

The diameter of the elastomeric retention ring 110 has been predetermined to be slightly less than the outside diameter of that portion of the conical surface 24 which aligns with second end 108 of tonometer cover 100 when the surfaces 102 and 22 are in contiguous contact. Retention ring 110 further provides means for handling tonometer cover 100 during application and removal from the applanation tonometer head 20.

Referring now to FIG. 4, there is shown a second alternate embodiment of applanation tonometer cover 100. In this embodiment, retention ring 120 secures the tonometer cover 100 to the applanation head 20. Retention ring 120 is formed by a ring having an internal conical surface adapted to substantially match that of surface 24 of tonometer applanation head 20. Tonometer cover 100 is applied to the applanation tonometer head 20 as has been previously described. Although not shown, the embodiment of FIG. 4 may include tab members 130 to facilitate handling tonometer cover 100 during application to and removal from applanation head 20.

Retention ring 120 comprises an annular ring having a conical bore 122 extending from a first end 124 to a second end 126, where first end 124 has a larger internal diameter than second end 126. The external surface of retention ring 120 may be conically shaped to match that of internal bore 122 to aid in identifying the first end 124 during assembly of retention ring 120 to tonometer cover 100 and applanation head 20.

Subsequent to application of tonometer cover 100 to applanation head 20, retention ring 120 is put in sliding engagement with tonometer applanation head 20. Retention ring 120 is applied to applanation head 20 with first end 124 of retention ring 120 facing applanation head 20, and then slid over the conical surfaces 24 and 104 of applanation head 20 and tonometer cover 100, until the conical internal bore 122 of retention ring 120 tightly engages the applanation head and cover combination. The internal diameters of first end 124 and second end 126 of retention ring 120 have been predetermined to approximate the external diameter of a section of the conical surface 24 of applanation head 20 located approximately 75% of the length of conical surface 24. In addition to lockingly engaging tonometer cover 100 to applanation head 20, retention ring 120 serves to stretch tonometer cover 100 slightly to provide a taut covering for the contact planar surface 22 of applanation head 20 with the substantially planar surface 102 of tonometer cover 100.

Referring to FIG. 5, there is shown an adaptation of the first embodiment shown in FIG. 2 wherein the tabs 130 provide both a means to handle tonometer cover 100 and a means to retain it n place on the applanation head 20. The means for retaining tonometer cover 100 may comprise a latch and hook type fastening system 150. Tab member 130 having an inner surface 132 on which is located a first material 152 having either latch or hook type members formed thereon. On the opposing surface 24 of applanation head 20 is located second material 154 having the other of said latch or hook type members formed thereon, thus forming the well-known Velcro ® releasable coupling system.

In the alternative, inner surface 132 of tab member 130 may be coated with a releasable type adhesive, or material 152 may be double-backed releasable adhesive strip, for use in coupling tonometer cover 100 to applanation head 20. Thus, the tab member 130 may perform the dual function of providing a means to handle tonometer cover 100 during application to applanation head 20 and during its removal, as well as providing a means for retaining tonometer cover 100 in place.

As is shown in FIGS. 1 and 2, tonometer cover 100 has been adapted for providing a protective disposable cover for application to the Goldmann-type applanation tonometer 10. Tonometer cover 100 has a preformed frusto-conical contour which dimensionally approximates the frusto-conical contour of applanation head 20. Thus, tonometer cover 100 forms a tightly fit sheath over applanation head 20 with substantially planar surface 102 of tonometer cover 100 fitting tightly across the substantially planar surface 22 of applanation head 20, such that the optical examination of patient's cornea 30 is unimpeded. It is therefore important that the tonometer cover 100 in general and the substantially planar surface 102 in particular be optically transparent and sufficiently thin such that neither the optics of the instrument nor the force measurement are interfered with. Therefore, it is important that tonometer cover 100 have a contour which allows for substantially continuous interface with Goldmann-type applanation head 20 such that the optically transparent material from which tonometer cover 100 is composed will form a distortion free window through which the cornea 30 can be clinically observed.

Another important feature of tonometer cover 100 is the tab member 130 which provides a means for handling tonometer cover 100 without coming in contact with the surface 102 which is to contact, or has contacted, the cornea 30 of a patient 40. Tonometer cover 100 may be provided as a sterile sheath, as will be described in following paragraphs, thus enhancing the importance of having one or more tab members 130 for handling tonometer cover 100 without contaminating the sterile field around surface 102. It is an equally important feature of tab members 130 to provide a means for removing tonometer cover 100 from applanation head 20 without contacting the surface 102 which has been contaminated by the lacrimal fluid from the surface of the cornea 30. Thus, tonometer cover 100 provides a protective sheath for the Goldmann-type applanation tonometer 10 to prevent applanation head 20 from being a means for transmitting communicable diseases from one patient to another. Further, the tab members 130 provide a safe means for handling tonometer cover 100 to prevent it from becoming a means for transmitting communicable disease between a patient 40 and the medical staff administering the test.

As shown in FIG. 6, tonometer cover 100 may be sterilized and maintained in a sterile condition until required for use within a package 160. Package 160 may be formed from any of a number of materials capable of providing a sterile enclosure for tonometer cover 100. Package 160 is provided with at least one score line 164 to provide a means to easily separate at least a portion 162 of at least one wall of package 160. Subsequent to the separation of wall portion 162 from package 160, tonometer cover 100 can be removed by grasping the tab member 130 and applying tonometer cover 100 to applanation head 20, as has been previously described. Package 160 may be provided with two compartments (not shown), one compartment for tonometer cover 100 and a second compartment for the means for retaining tonometer cover 100 to the applanation tonometer head 20. Thus, this second compartment may contain the double-backed removable adhesive strip 140 or the retaining ring 120.

Figure 8:
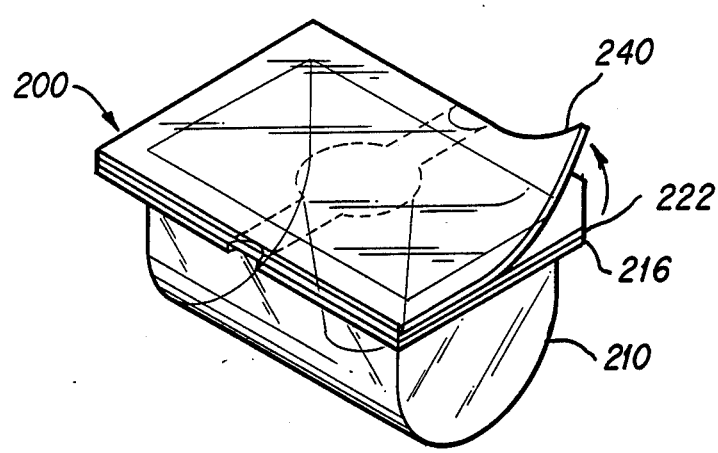
FIG. 8 is a perspective view of the sterile protective cover kit of FIG. 7; and, FIG. 9 is a perspective view of an alternate embodiment of the protective cover kit of FIG. 7.

Referring now to FIGS. 7 and 8, there is shown an alternate packaging system for applanation tonometer cover 100 wherein one wall of package 200 has tonometer cover 100 formed therein. The package assembly 200 comprises a package housing member 210 which forms a cavity into which the preformed contour of tonometer cover 100 can extend. Tonometer cover 100 is formed in sheet 220 which forms the closure wall for package housing 210. Closure wall 220 may be coupled to package housing 210 by any of a plurality of well-known techniques such as adhesive bonding or heat sealing. To accomodate the bonding of closure wall 220 to package housing member 210, package housing member 210 includes flange members 212 located on the periphery around the cavity 205 formed by housing member 210. Closure wall 220 with tonometer cover 100 formed therein can thus provide a sterile package for the exterior surface of tonometer cover 100 contained within the cavity formed in package housing member 210.

The second end 108 of tonometer cover 100 and tab members 130 are defined by a plurality of perforations 230 in closure wall 220. This series of perforations 230 provides the means by which tonometer cover 100 can be easily separated from closure wall 220. To further facilitate the removal of tonometer cover 100 by tab members 130, opposing flange members 212A have cut-outs 214 formed therein. With tab members 130 located above cut-outs 214, it becomes a simple matter to remove tonometer cover 100 from the package 200. This is accomplished by simply grasping tab member 130 and pulling it free of closure wall member 220.

Package assembly 200 further includes a peel-off protective flap or lid member 240 for providing a removable protective seal and closure for package 200. Peel-off flap 240 maintains the sterile environment within the cavity 205 formed by package housing member 210, which would otherwise be compromised by the perforations 230 formed in closure wall 220. In addition, the peel-off flap 240 protects the interior surface of tonometer cover 100 from dust and dirt which might accumulate therein, prior to use.

Peel-off protective flap 240 overlays the closure wall 220 and is releasably coupled thereto by techniques, such as releasable adhesive or other like methods well-known in the packaging art. To facilitate the removal of flap 240 from the remainder of package 200, housing member 210 and closure wall 220 include overlapping clipped corners 216 and 222, respectively. This arrangement permits the corner 242 of protective flap 240 to extend beyond both closure wall 220 and housing member 210 at clipped corners 222 and 216, respectively, allowing protective flap 240 to be easily grasped and pulled free of the remainder of package 200.

Figure 9:
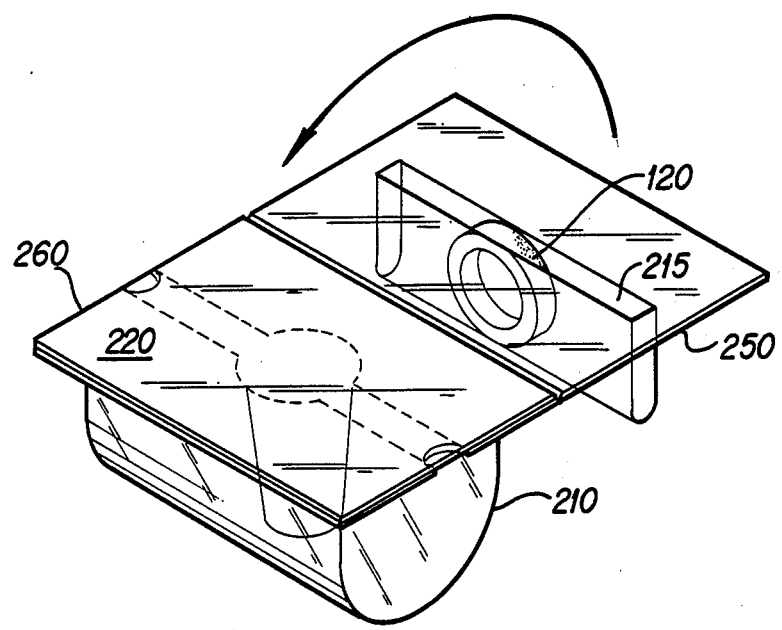

When it is required that tonometer cover 100 include a retention means such as double-backed releasable adhesive strip 140 or retaining ring 120, package 200 may include a second cavity 215 formed integrally into housing member 210 as shown in FIG. 9. In this embodiment, the protective flap is provided by the housing member portion 250, having cavity 215 formed therein. Housing member portion 250 is folded over the housing member portion 260 and releasably sealed to provide the final closure for the package.

Package assembly 200 provides a novel kit for providing a protective tonometer cover for use on a Goldmann-type applanation tonometer 10. The disposable, sterile, optically transparent, and thin tonometer cover 100 is formed in one wall 220 of the package assembly 200. The tonometer cover 100 with the tab members 130 formed thereon, are easily separable from the wall 220 by means of a plurality of perforations 230 which outline the end 108 of tonometer cover 100 and tabs 130. As shown, the housing member 210 includes flanges 212 which are adapted with cut-outs 214 to permit easy access for grasping tab members 130 and exerting force thereon to separate the tonometer cover 100 from the remainder of wall 220. Package 200 further includes a protective peel-off flap 240 for maintaining sterile conditions within the cavity 205 formed in the housing member 210, and protects the interior surfaces of tonometer cover from contamination by foreign bodies, such as dust and dirt.

Although this invention has been described in connection with specific forms and embodiments thereof, it will be appreciated that various modifications other than those discussed above may be resorted to without departing from the spirit or scope of the invention. For example, equivalent elements may be substituted for those specifically shown and described, certain features may be used independently of other features, and in certain cases, particular locations of elements may be reversed or interposed, all without departing from the spirit or scope of the invention as defined in the appended Claims.

What is claimed is:

1. A disposable protective cover for application to an applanation tonometer head having a substantially frusto-conical contour defining opposing ends having a smaller diameter end and a larger diameter end including a substantially planar surface bounded by a conical surface, comprising:

a. a sheath member having a predetermined contour for contiguous interface with said tonometer head, said sheath being formed from a substantially optically transparent composition having a predetermined thickness for minimizing tonometer measurement interference, said sheath member being formed of a plastic composition and pre-formed into a substantially frusto-conical contour having a thickness dimension within the approximate range of 0.00025 to 0.002 inches, said sheath member being inserted on said tonometer head in a predetermined direction;

b. releasable retention means for releasably coupling said sheath member to said conical surface of said tonometer head, said releasable retention means including a retaining ring having an internal conical surface insertable on said tonometer head for clampingly retaining said sheath member between said retaining ring and said conical surface of said tonometer head, said retaining ring having an increasing internal diameter for insertion on and frictional engagement with said tonometer head when said retaining ring is slidingly engaged with said tonometer head in said predetermined direction extending between said tonometer head smaller diameter end and said larger diameter end; whereby said sheath member is sufficiently stretched by said insertion of said retaining ring on said tonometer head to provide a taut covering for said planar surface of said tonometer head.

2. The disposable protective cover as recited in claim 1 wherein said sheath member includes at least one tab formed thereon.

3. The disposable protective cover as recited in claim 1 wherein said disposable protective cover is enclosed by a package having at least one wall member removable therefrom.

4. A kit for providing a sterile cover for an applanation tonometer head, said tonometer head having a substantially planar portion bounded by a conical surface, comprising:

a. package means having a sterile interior for enclosing a sheath member, said sheath member having a substantially frusto-conical contour for covering said flat portion of said tonometer head and at least a portion of said conical surface, said sheath member having at least one tab member and being formed by a thin, optically transparent, plastic composition, said sheath member having a thickness dimension within the approximate range of 0.00025 to 0.002 inches, said package means having one wall member wherein a portion of said wall member is formed integrally in one-piece formation with said sheath member;

b. releasable retention means for releasably coupling said sheath member to said conical surface of said tonometer head, said retention means being enclosed within said package means.

5. The disposable protective cover as recited in claim 4 wherein said retention means includes an elastomeric band fixedly coupled to said sheath member for frictionally coupling said sheath member to said conical surface of said tonometer head.

6. The disposable protective cover as recited in claim 4 wherein said retention means is fixedly coupled to said tab.

7. The disposable protective cover as recited in claim 6 wherein said retention means comprises a latch and hook fastener having at least one latch member and at least one hook member, one of said latch or hook members being fixedly coupled to said conical surface of said tonometer head and the other of said members being fixedly coupled to said tab.

8. The disposable protective cover as recited in claim 6 wherein said retention means includes a double-backed removable adhesive tape strip for providing said releasable coupling of said sheath member to said conical surface of said tonometer head.

9. The disposable protective cover as recited in claim 6 wherein said retention means includes a removable adhesive coating.

10. The kit as recited in claim 4 wherein said package means further includes at least one package housing member for containing said sheath member therein.

11. The kit as recited in claim 10 wherein said package means includes a shield member releasably coupled to said wall member for protecting an interior portion of said sheath member.

12. The kit as recited in claim 10 wherein said wall member includes a perforation surrounding said sheath member to permit separation of said sheath member from said wall member.

13. A method of providing a sterile and disposable protective cover over a contact portion of an applanation tonometer head, said protective cover being provided from within a package having a removable wall and an underlying wall, comprising:
  a. locating said protective cover within said package, said protective cover defining a sheath member being formed of a plastic composition and preformed into a substantially frusto-conical contour having a thickness dimension within the approximate range of 0.00025 to 0.002 inches;
  b. removing at least a portion of said removable wall from said package;
  c. removing said protective cover from said package by grasping at least one tab member formed on said protective cover and separating said protective cover from a portion of said underlying wall of said package, said protective cover having been integrally formed in said underlying wall in one-piece formation;
  d. using said tab member as a handle, sliding said protective cover over said tonometer head until a substantially planar portion of said protective cover engages said contact portion of said tonometer head; and,
  e. releasably coupling said protective cover to said tonometer head.

14. The method according to claim 18 where the step of removing at least a portion of a wall from said package includes the step of removing a protective shield from said package to expose said protective cover.

* * * * *